United States Patent
Yamanobe et al.

[11] Patent Number: 6,127,160
[45] Date of Patent: Oct. 3, 2000

[54] PROTEIN HAVING CELLULASE ACTIVITIES AND PROCESS FOR PRODUCING THE SAME

[75] Inventors: Takashi Yamanobe, Ibaraki; Manabu Watanabe, Kanagawa; Toru Hamaya, Saitama; Naomi Sumida, Kanagawa; Kaoru Aoyagi, Kanagawa; Takeshi Murakami, Kanagawa, all of Japan

[73] Assignees: Japan as represented by Director General of Agency of Industrial Science and Technology; Meiji Seika Kaisha Ltd., both of Tokyo, Japan

[21] Appl. No.: 09/142,759

[22] PCT Filed: Mar. 14, 1997

[86] PCT No.: PCT/JP97/00824

§ 371 Date: Sep. 14, 1998

§ 102(e) Date: Sep. 14, 1998

[87] PCT Pub. No.: WO97/33982

PCT Pub. Date: Sep. 18, 1997

[30] Foreign Application Priority Data

Mar. 14, 1996 [JP] Japan .................................... 8-084479

[51] Int. Cl.[7] .................................................. C12N 9/42
[52] U.S. Cl. .................. 435/209; 435/320.1; 435/252.3; 435/254.1; 536/23.2
[58] Field of Search ....................... 536/23.2; 435/320.1, 435/252.3, 254.1, 209

[56] References Cited

U.S. PATENT DOCUMENTS 4,562,150 12/1985 Yamanobe et al. ....................... 435/99
4,894,338 1/1990 Knowles et al. ...................... 435/172.3

FOREIGN PATENT DOCUMENTS 59-166081 9/1984 Japan ................................ C12N 9/42
6-277088 10/1994 Japan ................................ C12P 21/02
85/04672 10/1985 WIPO ............................ C12N 15/00

OTHER PUBLICATIONS

Koivula et al, *Protein Eng.*, 9(8) :691–699 (1996).
Rouvinen et al, *Science*, 249:380–386 (1990).
Gene, vol. 63, No. 1 (1988), pp. 11–22.
Applied and Environmental Microbiology, vol. 62, No. 6 (1996).
Gene, vol. 51, No. 1 (1987), pp. 43–52.
Applied and Environmental Microbiology, vol. 60, No. 8 (1993), pp. 2779–2785.
Biotechnology (N.Y.), vol. 5, No. 3 (1987), pp. 274–276 & 278.
Curr. Genet., vol. 30, No. 1 (1996), pp. 56–61.
Applied and Environmental Microbiology, vol. 60, No. 12 (1994), pp. 4387–4393.

*Primary Examiner*—Rebecca E. Prouty
*Attorney, Agent, or Firm*—Sughrue, Mion, Zinn, Macpeak & Seas, PLLC

[57] ABSTRACT

The object of the present invention is to analyze the amino acid sequence of the protein constituting the cellulase system, to clone the gene coding for the components of the cellulase system, and to establish a technique of inserting a clonal gene into the above strain thereby to produce cellulase having enhanced avicellase activity. The present invention relates to a protein having a part or the whole of the amino acid sequence depicted in the sequence listing under SEQ ID NO:1 and possessing cellulase activity, a DNA coding for the protein, an expression vector containing the DNA, a microorganism as transformed by the expression vector, and a process for producing a protein having enhanced cellulase activity by using the microorganism.

10 Claims, 1 Drawing Sheet

PROTEIN HAVING CELLULASE ACTIVITIES AND PROCESS FOR PRODUCING THE SAME

TECHNICAL FIELD

This invention relates to a protein having cellulase activity and a process for producing the same. More particularly, it relates to a DNA coding for a protein having cellulase activity, an expression vector containing the DNA, a microorganism as transformed by the expression vector, and a process for producing a protein having enhanced cellulase activity by using the microorganism.

BACKGROUND ART

Cellulose is a principal component constituting plants and widely exists in nature. Because cellulose is a hardly decomposable high-molecular polysaccharide comprising a glucose recurring unit polymerized through a β-1,4-glycoside bond, development of cellulase that splits the glycoside bond of cellulose to facilitate efficient extraction of the glucose unit is essential to effective utilization of the cellulosic biomass.

The terminology "cellulase" is a generic name of a group of enzymes catalyzing an enzymatic reaction system in which cellulose is decomposed into glucose, cellobiose or cellooligosaccharides. Cellulase includes species called $C_1$ enzyme, $C_x$ enzyme, β-glucosidase, exo-β-glucanase, endo-β-glucanase, cellobiase, etc. according to their mode of action, but the details have not yet been made clear.

Utilization of biomass by use of cellulase has been studied. In particular, the oil crisis in the '70s gave occasion for technological development of effective utilization of plant biomass for constantly supplying raw materials of energy, industrial material, food, etc.

Further, cellulase has been on the market as an industrial enzyme preparation and used as a main component of various products, such as detergents, fiber treating agents, additives for feed, and digestants. Therefore cellulase is expected to be of great use in practice.

Under the above situation, the inventors of the present invention have previously studied enzymatic saccharification of cellulose and succeeded in isolating a fungi, *Acremonium cellulolyticus* Y-94 (deposited in National Institute of Bioscience & Human Technology, Agency of Industrial Science and Technology (located at 1–3, Higashi 1-chome, Tsukuba-shi, Ibaraki-ken 305, JAPAN) under an international deposit number FERM BP-5826 pursuant to Budapest Treaty which was transferred from the original deposit (FERM P-6867 deposited on Jan. 12, 1983) on Feb. 19, 1997), which is capable of producing cellulase as reported in Japanese Patent Publication No. 43954/85.

The cellulase produced by this strain is a complex enzyme system (hereinafter sometimes referred to as a cellulase system) comprised mainly of three enzyme groups; $C_1$ enzymes represented by avicellase or FPase, $C_x$ enzymes acting on carboxymethyl cellulose (CMC), and β-glycosidase acting on cellooligosaccharides, such as cellobiose. Natural cellulose can be completely decomposed ultimately to glucose by these enzyme groups acting in harmony. The properties of the above-described cellulase system are described in the above-cited publication.

The cellulase system is characterized in that it has higher β-glucosidase activity than the cellulase having the origin from so far isolated microorganisms belonging to the genus Trichoderma or Asperaillus, and is therefore more successful in decomposing cellulose to glucose. However, there is no information on the identification of the protein composing the cellulase system produced by *Acremonium cellulolyticus* Y-94, amino acid sequence of the protein, DNA sequence of the gene coding for the amino acid sequence, and the like.

DISCLOSURE OF INVENTION

The inventors of the present invention have continued extensive investigation in order to analyze the amino acid sequence of the protein constituting the cellulase system of the *Acremonium cellulolyticus* Y-94 stain, to clone the gene coding for the components of the cellulase system, and to establish a technique of inserting a clonal gene into the above strain thereby to produce cellulase having enhanced avicellase activity. As a result, they have succeeded in isolating a novel and highly useful cellulase gene from the Y-94 strain and introducing the gene into a microorganism to induce transformation thereby making it possible to obtain cellulase in large quantity as gene expression, and thus completed the present invention.

The present invention relates to a protein having a part or the whole of the amino acid sequence depicted in the sequence listing under SEQ ID NO:1 and possessing cellulose activity; a DNA coding for the protein; a DNA sequence having a part or the whole of the DNA sequence depicted in the sequence listing under SEQ ID NO:2; an expression vector containing the DNA; a microorganism as transformed by the expression vector; and a process for producing a protein having cellulase activity by using the microorganism.

The protein having cellulase activity according to the invention has the amino acid sequence depicted in the sequence listing under SEQ ID:1. This protein derives its origin from the above-described fungi belonging to the genus Acremonium. The protein having the sequence of from the 21st amino acid to the 457th-amino acid depicted in the sequence listing under SEQ ID:1 is maturation protein, which will be sometimes called cellulose ACC2. The gene of cellulase ACC2 will be sometimes called cellulase ACC2 gene. The sequence of from No. 1 to No. 20 shown in the sequence listing under SEQ ID:1 is considered to be a signal peptide.

Cellulase ACC2 acts on highly crystalline insoluble cellulose, such as avicel, to produce reducing sugars, such as glucose and cellobiose. It has a molecular weight of about 63 KD (kilodalton) as measured by SDS polyacrylamide gel electrophoresis (hereinafter abbreviated as SDS-PAGE) and an isoelectric point at pI 4.8 and exhibits strong avicel decomposing action especially in an acidic region.

The proteins having a part of the amino acid sequence depicted in the sequence listing under SEQ ID:1 are also included in the protein of the present invention. Such proteins include those having the amino acid sequence modified by addition, insertion, deletion, deficiency or substitution of some amino acid residues and still possessing cellulase activity.

Specific examples of the protein having cellulose activity according to the invention include the one having the amino acid sequence of from No. 21 to No. 457 shown in the sequence listing under SEQ ID:1 and the one having the amino acid sequence of from No. 21 to No. 457 shown in the sequence listing under SEQ ID:1 with the amino acid sequence of from No. 1 to No. 20 added to the N terminus thereof.

The amino acid sequence of the above-described protein can be determined as follows.

(1) Purification of Cellulase ACC2

Acremonium cellulolyticus Y-94 is cultured, and a fraction having avicellase activity of the culture is purified to such an extent that the resulting cellulase ACC2 fraction shows a single band in SDS-PAGE.

(2) Determination of N-Terminal and Internal Amino Acid Residues

Cellulase ACC2 obtained in (1) above is treated with various proteolytic enzymes (i.e., proteinase and peptidase), and the amino acid sequence of the resulting peptides was determined by means of an amino acid sequencer.

Comparing the thus determined amino acid sequence of the protein having cellulase activity with those of other cellulase species registered in *Protein Identification Resource* (*PIR*) R44.0, March, 1995, there is found no protein having the same amino acid sequence, providing confirmation that the protein is novel.

The present invention provides a DNA coding for the amino acid sequence of the above protein. The DNA is typically a part or the whole of the DNA sequence depicted in the sequence listing under SEC ID NO:2.

The DNA sequence depicted in the sequence listing under SEQ ID:2 derives its origin from the chromosomal DNA of Acremonium cellulolyticus and having an open reading frame (ORF) starting from the 241st ATG and stopping at the 1941st TAG.

The sequence of from the 301st to 1938th bases corresponds to the aforesaid maturation protein composed of 437 amino acid residues. It has been confirmed that there are 5 introns in the DNA sequence depicted in the sequence listing under SEQ ID:2 (see Example 7 hereinafter given).

Once the amino acid sequence of a protein is given, the DNA sequences which code for the amino acid sequence can easily be presumed, and an appropriate DNA sequence can be chosen from various DNA sequences coding for the whole or a part of the amino acid sequence depicted in the sequence listing under SEQ ID:1. Accordingly, the "DNA coding for a part or the whole of the amino acid sequence depicted in the sequence listing under SEQ ID:1" includes not only DNA having a part or the whole of the DNA sequence depicted in the sequence listing under SEQ ID:2 but also DNA having different codons coding for the same amino acid (degenerate codons).

The DNA sequence of the gene coding for the protein having cellulase activity according to the invention differs from any of those of cellulase genes which have been so far cloned and analyzed. This fact has been confirmed by comparison with cellulase genes registered at the nucleic acid data base, GenBank (registered trade name), R88.0, April, 1995.

The DNA having the above described DNA sequence may have its origin from nature or may be synthetic. Synthesis of the DNA may be carried out by making use of part of naturally-occurring DNA.

The DNA can typically be obtained from the genomic library or cDNA library of *Acremonium cellulolyticus* origin by methods commonly used in the field of genetic engineering, for example, by a screening method using an appropriate DNA probe prepared on the basis of the information of a partial amino acid sequence. The DNA can also be obtained from the above-described deposited strain.

The DNA according to the present invention can be determined as follows.

(1) Preparation of DNA Probe for Cloning

Acremonium cellulolyticus Y-94 is cultivated, and produced cellulase is purified through various chromatographic techniques taking cellulase activity as a measure. Then, the purified cellulase is decomposed by various proteolytic enzymes, and the amino acid sequence of the resulting peptides is determined on an amino acid sequencer.

A mixture of oligonucleotides which contains all the DNA sequences predicted from the determined amino acid sequences is prepared. The DNA sequences are amplified by the polymerase chain reaction (PCR) method. The resulting oligonucleotide is used as a probe.

(2) Preparation of Genomic DNA Library

Acremonium cellulolyticus Y-94 is cultured, and the whole DNA is prepared from the collected microbial cells. The resulting DNA is digested by a restriction enzyme. A genomic phage library is prepared using the resulting DNA.

(3) Cloning of Cellulase Gene

The library prepared in (2) above and the PCR-amplified fragment are hybridized, and positive plaques are selected.

(4) Determination of DNA sequence

The thus selected phage clone is sub-cloned in a vector for *E. coli,* and the DNA sequence of the DNA is determined on a DNA sequencer.

Further, mRNA obtained from *Acremonium cellulolyticus* Y-94 is treated with a reverse transcriptase to synthesize cDNA, and the cDNA of ACC2 gene is obtained by the PCR method. Comparison between the total DNA sequence of the cDNA and the above-described DNA sequence of the genom reveals the existence of introns and the reading frame (see Example 7 and SEQ ID NO:2 in the sequence listing).

The present invention provides an expression vector which can replicate the above DNA of the invention in a host microorganism and contains the protein coded by this DNA in a condition capable of being expressed. The present invention also provides a microorganism transformed by the expression vector.

The host-vector system is not particularly limited. For example, systems using *E. coli,* ray fungi, yeast, mold, etc. and fused protein expression systems of the host protein and another protein can be used. Suitable host microorganisms include *E. coli,* yeast of the genus Saccharomyces, and fungus of the genus Trichoderma, Aspergillus or Acremonium. Useful vectors include plasmids capable of autonomous replication in *E. coli,* such as pBR322, pUC (preferably pUC18), and pBluescript, and those capable of autonomous replication in yeast, such as pYEUra3.

The vector of the present invention can be obtained by the methods and procedures commonly employed in genetic engineering.

In order for the expression vector of the invention to be introduced into a host microorganism and to express the desired protein, the expression vector may have a DNA for expression control or a genetic marker for selecting the microorganism in addition to the DNA of the present invention.

Since the DNA sequence depicted in the sequence listing under SEQ ID:2 is believed to contain such a regulatory sequence, etc., use of this DNA sequence as such seems to be advantageous in some cases.

The expression vector may contain the DNA coding for cellulose in tandem repeat. These sequences can be made exist in the expression vector in a conventional manner. The transformation of a microorganism by the vector can be conducted in a usual manner. For example, cellulase ACC2 gene is made into a plasmid together with a selective genetic marker, and the resulting plasmid is introduced into *Acremonium cellulolyticus* by protoplast. The resulting transformant is resistant to the selected marker and improved cellulase activity.

The thus obtained transformant is cultured in an appropriate medium, and the protein of the present invention can be isolated from the culture. Cultivation conditions for the transformant are appropriately decided according to the microorganism used. Recovery and purification of the protein from the culture can be carried out in a usual manner.

BEST MODE FOR CARRYING OUT INVENTION

Figure 1:
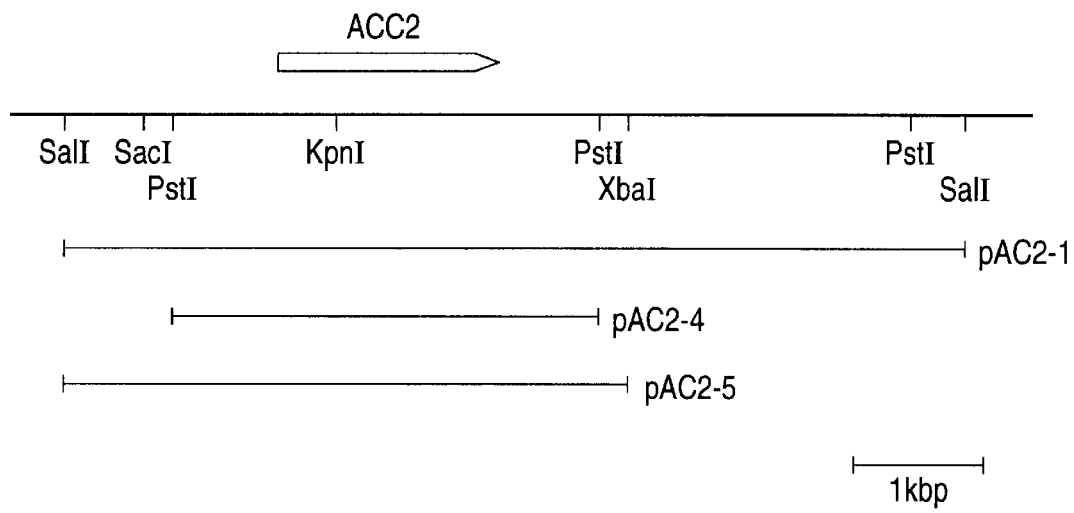
FIG. 1 is a restriction map of a 7 kbp SalI-digested fragment.

The present invention will now be illustrated in greater detail by way of Examples, but it should be understood that the invention is not construed as being limited thereto.

EXAMPLE 1

Purification of Cellulase ACC2

*Acremonium cellulolyticus* Y-94 (FERM BP-5826) was cultured in a cellulase-inducing medium (4% cellulose; 1% Bacto Peptone; 0.6% potassium nitrate; 0.2% urea; 0.16% potassium chloride; 0.12% magnesium sulfate; 1.2% potassium primary phosphate; 0.001% zinc sulfate; 0.001% manganese sulfate; 0.001% copper sulfate (pH 4.0)). The culture was centrifuged, and the supernatant was spray-dried to obtain crude cellulase powder. The powder (50 g) was dissolved in water (500 ml) and filtered through a membrane filter of 0.45 μm.

The resulting enzyme solution was passed through Q Sepharose High Performance Column (60×100 mm) equilibrated with a 5 mM acetate buffer (pH 5.8) using Biopilot System (manufactured by Pharmacia Biotec). The enzyme solution was adsorbed under the above buffered condition, and the non-adsorbed fraction was taken as fraction 1. Fraction 1 was desalted and concentrated by ultrafiltration (fractionated molecular weight: 5000) and freeze-dried.

Freeze-dried fraction 1 was dissolved in a 20 mM tris-acetic acid buffer (pH 7.4) containing 1.2 M ammonium sulfate, followed by filtration through the same membrane filter as used above. The filtrate was again passed through the above column and eluted with a 20 mM tris-acetic acid buffer (pH 7.4) having an ammonium sulfate concentration gradient. The fraction exhibiting avicellase activity (ammonium sulfate concentration: 0.3 to 0.5 M) was collected. The fraction showed a nearly single band of protein ACC2 having a molecular weight of about 63 KD in SDS-PAGE.

EXAMPLE 2

1) Determination of N-Terminal Amino Acid Sequence

The purified protein (ACC2) obtained in Example 1 was treated with bovine liver pyroglutamic acid aminopeptidase (available from Boehringer Mannheim) in accordance with the method of Podell, D. N. et al. (Podell, D. N. et al., *Biochem. Biophys. Res. Commun.* Vol. 81, p. 176 (1978) to remove the modified N-terminal residue, and the next 9 amino acid residues on the N-terminus side were determined by means of a protein sequencer Model 492 (manufactured by Perkin-Elmer). The 9-amino acid sequence is shown in SEQ ID NO:3 in the sequence listing.

(2) Peptide Mapping

In order to determine the internal amino acid sequence of the protein, the protein obtained in Example 1 (freeze-dried) was treated with V8 Protease (produced by Wako Pure Chemical Industries, Ltd.) in a 50 mM ammonium bicarbonate buffer (pH 7.8), lysyl endopeptidase (produced by Seikagaku Corporation) in a 25 mM tris-HCl buffer (pH 9.0), and trypsin (produced by Sigma) in a 100 mM ammonium bicarbonate buffer (pH 8.0). Each reaction was conducted at 37° C. overnight. Each enzyme was used in an amount of about 1/50 mol-substrate.

The decomposition product was subjected to column chromatography (column: C8 220×2.1 mm) using Model 172μ Preparative HPLC System (manufactured by Perkin-Elmer). Gradient elution was conducted with water-acetonitrile (5 to 35%) to obtain 7 kinds of peptides. The amino acid sequence of each peptide was determined with protein sequencer Model 492. The resulting sequences are shown in SEQ ID NO:4 through 10 in the sequence listing.

These amino acid sequences showed homology to the amino acid sequence of cellobiohydrase II (cbh-II) protein produced by *Trichoderma reesei* (Chung Mong Cen et al., *Bio/Technology*, Vol. 5, pp. 274–278 (1987)), which strongly suggests that the above protein is one kind of cellulase.

Further, the above sequences were compared with those of other cellulase species registered at Protein Identification Resource (PIR) R44.0 (Mar., 1995). Some registered sequences (e.g., cbh-II) were homologous but not identical with these sequences, providing confirmation that the above protein is novel.

EXAMPLE 3

(1) Isolation of Genomic DNA

*Acremonium cellulolyticus* Y-94 (FERM BP-5826) was cultured in an (S) medium (2% bouillon; 0.5% yeast extract; 2% glucose) at 32° C. for 2 days, and the microbial cells were collected by centrifugal separation. The cells were freezed with liquid nitrogen and ground in a homogenizer AM-3 (manufactured by Nihon Seiki K.K.). The ground cells were suspended in a TE buffer (10 mM tris-HCl buffer (pH 8.0), 1 mM EDTA) containing 1% SDS and kept at 65° C. for 30 minutes. The system was treated with phenol, precipitated in ethanol, treated with proteinase K and ribonuclease A, and subjected to separation in a preparative ultracentrifuge 65P-7 (manufactured by Hitachi Koki Co., Ltd.) according to cesium chloride density-gradient centrifugation method to obtain DNA.

(2) Preparation of Primer

Primers corresponding to the 1st to the 5th amino acid residues of peptide Lys-39 (SEQ ID NO:9 in the sequence listing) and the 1st to the 6th amino acid residues of peptide Trp-30 (SEQ ID NO:10 in the sequence listing) were synthesized. That is, predicting that peptide Lys-39 is positioned closer to the N-terminus than peptide Trp-30 based on the report of Chung Mong Cen et al. (Chung Mong Cen et al., *Bio/Technology*, Vol. 5, pp. 274–278 (1987), oligonucleotides having each of the sequences shown in the sequence listing under SEQ ID NO:11 through 16 were synthesized. The primers for the DNA corresponding to peptide Lys-39 were synthesized from the nucleotides corresponding to lysine, the amino acid recognized by lysyl endopeptidase.

(3) Preparation of Long-chain Probe by PCR Method

Long-chain DNA probe was prepared by PCR amplification using the whole DNA of *Acremonium cellulolyticus* Y-94 (FERM BP-5826) prepared in (1) above as a template.

PCR was performed as follows. To 1 μg of the genomic DNA obtained in (1) above was added 1 FM of each of the primers prepared in (2) above, and the DNA was denatured at 94° C. for 10 minutes in the presence of dNTP. Thereafter, Taq DNA polymerase (Recombinant Taq, produced by Takara Shuzo Co., Ltd.) was added thereto, and the system was subjected to a replication cycle of 94° C.×1 minute, 55° C.×2 minutes, and 72° C.×3 minutes. The replication cycle was repeated 30 times. As a result, DNA comprising 500 bp having a combination of Lys-39B (SEQ ID NO:12 in the sequence listing) and Trp-30A (SEQ ID NO:13 in the sequence listing) or a combination of Lys-39B and Trp-30B (SEQ ID NO:14 in the sequence listing) was specifically amplified. The resulting DNA fragment was used as a probe in the subsequent screening.

EXAMPLE 4

Preparation of Genomic DNA Library

The genomic DNA of Acremonium cellulolyticus Y-94 (FERM BP-5826) prepared in Example 3 was partially digested with Sau3AI. The resulting DNA fragment was ligated to BamHI arm of a phage vector, λEMBL3 cloning kit (produced by Stratagene) by using T4 ligase (Ligation Kit Ver. 2, produced by Takara Shuzo Co., Ltd.). The ligated DNA was precipitated in ethanol and dissolved in a TE buffer. The whole amount of the ligated mixture was subjected to phage packaging using Giga Pack II Packaging Kit (produced by Stratagene) to form infectious phage particles. The resulting phase was inoculated to E. coli XL1-Blue MRA (P2).

Cloning of a purposed gene was carried out using the resulting library of $7.5 \times 10^4$ phage particles.

EXAMPLE 5

Cloning of Cellulase ACC2 Gene (1) Screening by Plaque Hybridization

The PCR-amplified DNA fragment of 500 bp obtained in Example 3 was previously labeled in accordance with ECL Direct System (produced by Amersham).

The phage plaques formed in Example 4 were transferred to Hibond N+ Nylon Transfer Membrane (produced by Amersham), denatured with an alkali, washed with SSC having a 5-fold concentration (SSC: 15 mM sodium tertiary citrate; 150 mM sodium chloride), and dried to immobilize the DNA to the nylon membrane. In accordance with the instructions of the kit, after pre-hybridization (42° C.×1 hour), the labeled DNA probe was added thereto to conduct hybridization at 42° C. for 4 hours. The probe was washed according to the instructions of the kit.

The washed nylon membrane was immersed in the detecting solution attached to the kit for 1 minute and then contacted with Hyper Film ECL of the same manufacturer. The film was exposed to light and developed to obtain 4 positive clones.

(2) Preparation of Phage DNA

DNA was prepared from the positive clones in accordance with the method of Maniatis, et al (J. Sambrook, E. F. Fritsch and T. Maniatis, *Molecular Cloning,* Cold Spring Harbor Laboratory Press (1989)).

LE392 as a host E. coli was cultured in an LB medium (1% Bacto Trypton; 0.5% yeast extract; 0.5% sodium chloride) overnight and infected with a solution of a phase of single plaque origin, followed by further culturing in an LB medium overnight. To the culture were added 1M sodium chloride and 0.8% chloroform to accelerate the lysis of E. coli. The culture was subjected to centrifugation to remove the residual microbial cells, and the phage particles were recovered by precipitation in polyethylene glycol (10% PEG 6000). The phage particles were treated with proteinase K (available from Wako Pure Chemical Industries, Ltd.) in the presence of SDS, extracted with phenol, and precipitated in ethanol to recover phage DNA.

The thus prepared DNA was analyzed by Southern blotting in according with ECL Direct System (produced by Amersham). As a result of hybridization using the PCR-amplified fragment of Example 3 as a probe, the SalI-digested fragment of 7 kbp was hybridized in common. The restriction map of the SalI-digested fragment is shown in FIG. 1.

The SalI fragment capable of hybridizing in common was subcloned in pUC18 (available from Takara Shuzo Co., Ltd.). The resulting plasmid is designated pAC2-1.

EXAMPLE 6

Determination of DNA Sequence

The DNA sequence was determined by use of A.L.F. DNA Sequencer II (manufactured by Pharmacia Biotec). Ready-mix Gel (produced by Pharmacia Biotec) or Long Ranger (produced by FMC) was used as a sequencing gel. Various reagents of A.L.F grade produced by Pharmacia Biotec (N,N,N',N'-tetramethylethylenediamine, urea, ammonium persulfate) were used for gel formation.

The reactions for DNA sequence analysis were carried out with Autoread Sequencing Kit (produced by Pharmacia Biotec). The conditions of gel formation, reaction conditions, and conditions of electrophoresis were designed by referring to the instructions of the kit.

The template plasmid (hereinafter simply referred to as a template) for sequence determination was prepared by digesting pAC2-1 with PstI, cloning the resulting PstI-digested fragment of 3.5 kbp using pUC118. The thus prepared plasmid (designated pAC2-4) is shown in FIG. 1.

The template was alkali-denatured with 2M sodium hydroxide and then annealed with ACC2-specific sequencing primer (WACC-01 to WACC-12) to conduct primer extension.

As a result of analysis on reaction products with the sequencer, the DNA sequence of 2196 bp out of the PstI-digested fragment was determined as shown in the sequence listing under SEQ ID NO:2.

The DNA sequences of the ACC2-specific sequencing primers (WACC-01 to WACC-12) are shown in the sequence listing under SEQ ID NO:17 through 28.

EXAMPLE 7

Non-coding regions (introns) were determined by preparing mRNA from Acremonium cellulolyticus Y-94 (FERM BP-5826) in a usual manner, synthesizing cDNA by the action of reverse transcriptase, and comparing the DNA sequence of the cDNA with that of chromosomes.

(1) Preparation of Whole RNA

Acremonium cellulolyticus Y-94 (FERM BP-5826) was cultured in a cellulase-inducing medium, preferably the above-described (S) medium containing cellulose (5% Funacel, produced by Funakoshi K.K.), at 32° C. for 2 days. After completion of the culturing, the culture was centrifuged (3500 rpm×10 minutes) to collect the microbial cells. The cells were washed with sterilized water, freezed with liquid nitrogen, and ground in a blender.

The ground cells were suspended in a denaturing solution containing 4 M guanidine thiocyanate (4M guanidine thiocyanate; 25 mM sodium tertiary citrate; 0.5% sodium N-laurylsarcosinate; 0.1 M mercaptoethanol). After stirring at room temperature for several minutes, the cell suspension was neutralized with 2 M sodium acetate (pH 4.5). TE-saturated phenol was then added, followed by stirring. Chloroform-isoamyl alcohol (24:1) was added thereto, followed by stirring. The system was centrifuged (3500 rpm× 10 minutes) to remove the phenol-denatured cells. The upper layer (aqueous layer) was recovered, and the nucleic acid was precipitated in isopropyl alcohol. The precipitate was collected by centrifugation (3500 rpm×10 minutes), resuspended in 70% ethanol/water, and again centrifuged to wash the precipitate.

The precipitate was dissolved in a TE buffer to a nucleic acid concentration of 1 mg/ml and re-precipitated in 2.5 M lithium chloride (5° C.×2 hours). The precipitate was collected by centrifugation (12000 rpm×10 minutes) and washed with 70% ethanol to obtain a whole RNA fraction.

(2) Preparation of Poly-A Tail-Added RNA (=mRNA)

mRNA was prepared by using mRNA Purification Kit (produced by Pharmacia Biotec) as follows.

One milligram of the whole RNA obtained in (1) above was dissolved in 1 ml of an elution buffer, thermally denatured at 65° C. for 10 minutes, and rapidly cooled in ice. To the solution was added 0.2 ml of a sample buffer. The whole amount of the RNA solution was passed through an oligo(dT) cellulose column. After washing the column successively with a high salt buffer three times and with a low salt buffer three times, the column was eluted with the elution buffer heated at 65° C. These operations were repeated once more to obtain an mRNA fraction.

(3) Synthesis of cDNA cDNA was synthesized by using Time Saver cDNA Synthesis Kit (produced by Pharmacia Biotec) as follows.

In 20 $\mu$l of a sample buffer was dissolved 5 $\mu$g of the mRNA and heated at 65° C. for 10 minutes. The solution was added to First Strand Synthesis Mix together with a dithiothreitol solution and an oligo(dT) as a primer and allowed to react at 37° C. for 1 hour. The whole amount of the system was added to Second Strand Mix and allowed to react at 12° C. for 30 minutes and then at 22° C. for 1 hour to obtain cDNA.

(4) Amplification of cDNA of Cellulase ACC2 by PCR Method

The cDNA of ACC2 was amplified by the PCR method using the whole cDNA as a template. PCR was conducted by using LA PCR Kit (produced by Takara Shuzo Co., Ltd.). The cDNA and primers, ACC2n-Stu and ACC2c-Xho, were subjected to a replication cycle of 94° C.×1 minute, 55° C.×2 minutes, and 720C×2 minutes. The replication cycle was repeated 25 times to amplify cDNA of ACC2 having about 1.5 kbp.

The DNA sequence of the primers, ACC2n-Stu and ACC2c-Sho, is shown in the sequence listing under SEQ ID NO:29 and SEQ ID NO:30.

The PCR-amplified fragment was subjected to agarose gel electrophoresis, recovered from agarose gel by means of Band Prep Kit (produced by Pharmacia Biotec), and cloned in pT7-Blue (produced by Novagen). The resulting plasmid, pACc2-1, was used as a template for intron determination.

(5) Determination of DNA sequence of cDNA

The sequencing reactions were carried out with the above-mentioned Autoread Sequencing Kit. The plasmid pACc2-1 was alkali denatured with 2 M sodium hydroxide and precipitated in ethanol. "Universal" and "Reverse" attached to the kit, and WACC-02 and WACC-05 whose DNA sequences are depicted in the sequence listing under SEQ ID NO:18 and SEQ ID NO:21, respectively, were used as primers and extended in the presence of T7 polymerase using the alkali-denatured plasmid as a template.

As a result, it was revealed that there are 5 introns; 320 to 389 bp (Intron I), 459 to 516 bp (Intron II), 800 to 869 bp (Intron III), 1124 to 1198 bp (Intron IV), and 1598 to 1651 bp (Intron V).

The positions of the non-coding start sequence, non-coding stop sequence, and internal regulatory sequence of these introns are shown in Table 1 below.

TABLE 1

| Intron | Non-coding Start Sequence | Non-coding Stop Sequence | Regulatory Sequence |
|---|---|---|---|
| Intron I | 320–325 | 387–389 | 367–371 |
| Intron II | 459–464 | 514–516 | 496–500 |
| Intron III | 800–805 | 867–869 | 856–860 |
| Intron IV | 1124–1129 | 1196–1198 | 1177–1181 |
| Intron V | 1598–1603 | 1649–1651 | 1634–1638 |

EXAMPLE 8

Figure 2:
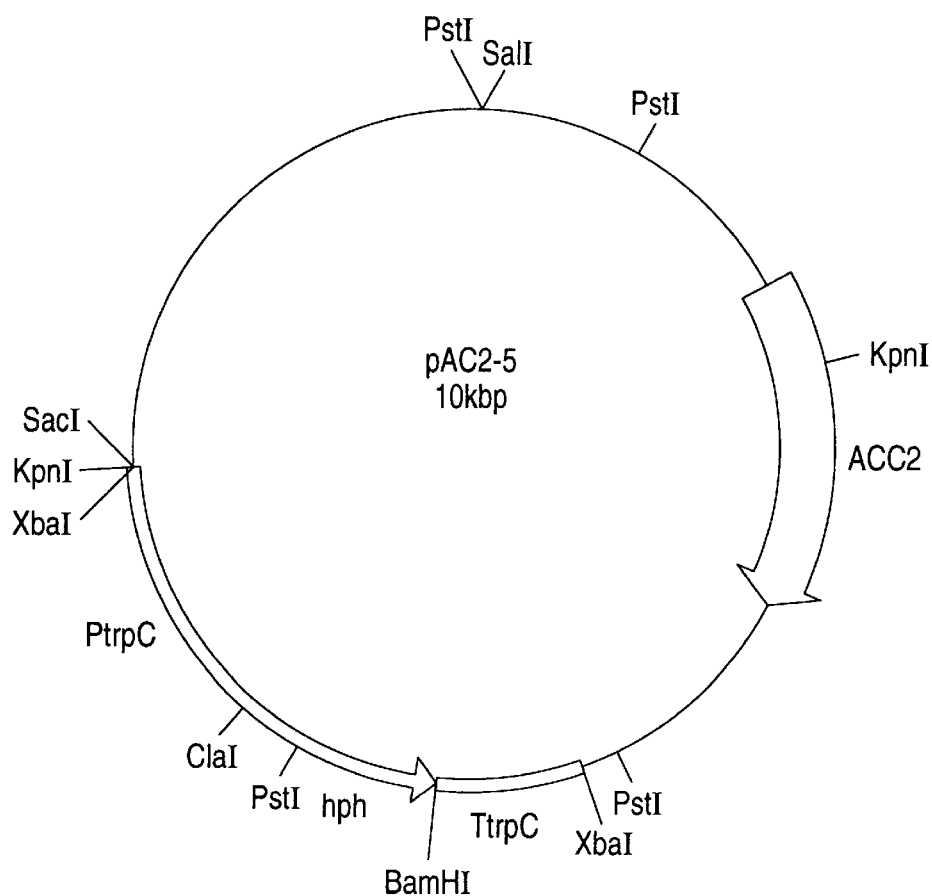
FIG. 2 shows the structure of plasmid pAC2-5.

In order to selfclone the ACC2 gene into *Acremonium cellulolyticus* Y-94 (FERM BP-5826), pAC2-1 was digested with XbaI, and a DNA fragment comprising 7.2 kbp was recovered. A Hygromycin B-resistant cassette of pDH25 origin (Cullen, D., Leong, S. A., Wilson, L. J. and Henner, D. J., *Gene*, Vol. 57, pp. 21–26 (1987)) was inserted to the fragment to prepare pAC2-5 as a vector for *Acremonium cellulolyticus* transformation (see FIG. 2).

EXAMPLE 9

Transformation of *Acremonium cellulolyticus*

*Acremonium cellulolyticus* Y-94 (FERM BP-5826) was cultivated in the above-described (S) medium at 32° C. After 24 hour-cultivation, the culture was centrifuged at 3000 rpm for 10 minutes to collect the microbial cells. The cells were washed with 0.5 M sucrose and suspended in a cell wall lytic enzyme solution (5 mg/ml Novozyme 234, 5 mg/ml Cellulase Onozuka-R-10, 0.5 M sucrose) having been filtered through a filter of 0.45 $\mu$m and shaken at 30° C. for 60 to 90 minutes to obtain protoplasts.

The resulting suspension was filtered and centrifuged at 2500 rpm for 10 minutes to collect the protoplasts, which were then washed with an SUTC buffer (0.5 M sucrose, 10 mM calcium chloride, 10 mM tris-HCl (pH 7.5)).

The protoplasts were suspended in 1 ml of an SUTC buffer. To 100 $\mu$l of the suspension was added 10 $\mu$l of a 1 $\mu$g/$\mu$l TE solution of the pAC2-5, and the system was allowed to stand on ice for 5 minutes. Then, 400 $\mu$l of a PEG solution (60 w/v % PEG 4000; 10 mM calcium chloride; 10 mM tris-HCl (pH 7.5)) was added thereto, and the system was allowed to stand on ice for 20 minutes. To the suspension was added 10 ml of an SUTC buffer, and the system was centrifuged at 2500 rpm for 10 minutes. The collected protoplasts were suspended in 1 ml of an SUTC buffer, followed by centrifugation at 4000 rpm for 5 minutes, and the collected protoplasts were finally suspended in 100 $\mu$l of an SUTC buffer.

The thus treated protoplasts were layered on an (A) medium (0.2% sodium nitrate; 0.1% dipotassium hydrogenphosphate; 0.05% potassium chloride; 0.05% magnesium sulfate heptahydrate; 0.001% iron sulfate heptahydrate; 17.1% sucrose; 1% Bacto Agar (pH 6.0)) containing 500 $\mu$g/ml of Hygromycin B together with a soft agar medium (0.2% sodium nitrate; 0.1% dipotassium hydrogenphosphate; 0.05% potassium chloride; 0.05% magnesium sulfate heptahydrate; 0.001% iron sulfate heptahydrate; 17.1% sucrose; 0.8% Bacto Agar (pH 6.0)) and cultured at 30° C. for 5 to 9 days. The colonies formed were taken as a transformant. Plasmid pAC2-5 was thus transformed into Acremonium cellulolyticus Y-94 (FERM BP-5826). There appeared about 2 colonies exhibiting Hygromycin B resistance per µg of the DNA.

EXAMPLE 10

Of the transformants obtained in Example 9 two strains exhibiting high Hygromycin B-resistance were cultured in the same cellulase-inducing medium as used in Example 1 at 32° C. for 7 days, and the culture was centrifuged. Analysis of the supernatant liquor by SDS-PAGE revealed that the both transformants secreted a higher amount of the ACC2 protein than the parent strain.

The cellulase activity was evaluated by measuring the avicel decomposing activity of the culture supernatant liquor in accordance with the method described in W. A. Wood, S. T. Kellogg, Methods in Enzymology, Vol. 160, p. 97, "Biomass part A, Cellulose and Hemicellulose", Academic Press. The results of measurement are shown in Table 2 below. As is apparent from the results, the transformants possessed improved cellulase activity. In particular, the specific activity of transformant 2 was 1.5 times that of the parent strain.

TABLE 2

| Strain | Avicel Decomposing Activity (%) |
| --- | --- |
| Transformant 1 | 109 |
| Transformant 2 | 159 |
| Parent strain | 100 |

INDUSTRIAL APPLICABILITY

Thus, the present invention reveals the amino acid sequence of a protein having cellulase activity and provides the DNA coding for the protein, an expression vector containing the DNA, a microorganism as transformed by the vector, and a process for producing a protein having cellulase activity using the microorganism.

The sequence listing in the present invention is shown below.

What is claimed is:

1. An isolated DNA molecule encoding the protein of SEQ ID NO:1 or a fragment thereof, wherein said fragment possesses cellulase activity.

2. An isolated DNA molecule according to claim 1, wherein said fragment comprises amino acids 21–457 of SEQ ID NO:1.

3. An isolated DNA molecule according to claim 2, wherein said DNA molecule comprises SEQ ID NO:2 or a fragment thereof.

4. An isolated DNA molecule according to claim 3, wherein said DNA molecule comprises nucleotides 301–1938 of SEQ ID NO:2.

5. An isolated DNA molecule according to claim 4, wherein said DNA molecule comprises nucleotides 241–1941 of SEQ ID NO:2.

6. An expression vector containing the DNA molecule described in any one of claims 1 to 5.

7. A microorganism obtained by transformation with the expression vector described in claim 6.

8. A microorganism according to claim 7, wherein said microorganism is a fungus belonging to the genus Acremonium.

9. A process for producing a protein having cellulase activity comprising culturing a microorganism described in claim 7 and collecting the cellulase from the culture.

10. A process for producing a protein having cellulase activity comprising culturing a microorganism described in claim 8 and collecting the cellulase from the culture.

* * * * *

```
                         SEQUENCE LISTING

<160> NUMBER OF SEQ ID NOS: 30

<210> SEQ ID NO 1
<211> LENGTH: 457
<212> TYPE: PRT
<213> ORGANISM: Acremonium cellulolyticus

<400> SEQUENCE: 1

Met Leu Arg Tyr Leu Ser Ile Val Ala Ala Thr Ala Ile Leu Thr Gly
 1               5                  10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Thr Ala Ala Ala
                85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
            180                 185                 190

Gly Glu Tyr Thr Val Ala Asn Asn Gly Val Ala Asn Tyr Lys Ala Tyr
        195                 200                 205
```

-continued

| | | | | | | | | | | | | | | |
|---|---|---|---|---|---|---|---|---|---|---|---|---|---|---|
|Ile|Asp|Ser|Ile|Val|Ala|Gln|Leu|Lys|Ala|Tyr|Pro|Asp|Val|His|Thr|
| |210| | | |215| | | |220| | | | | | |

Ile Leu Ile Ile Glu Pro Asp Ser Leu Ala Asn Met Val Thr Asn Leu
225                230                235                240

Ser Thr Ala Lys Cys Ala Glu Ala Gln Ser Ala Tyr Tyr Glu Cys Val
            245                250                255

Asn Tyr Ala Leu Ile Asn Leu Asn Leu Ala Asn Val Ala Met Tyr Ile
        260                265                270

Asp Ala Gly His Ala Gly Trp Leu Gly Trp Ser Ala Asn Leu Ser Pro
    275                280                285

Ala Ala Gln Leu Phe Ala Thr Val Tyr Lys Asn Ala Ser Ala Pro Ala
290                295                300

Ser Leu Arg Gly Leu Ala Thr Asn Val Ala Asn Tyr Asn Ala Trp Ser
305                310                315                320

Ile Ser Ser Pro Pro Ser Tyr Thr Ser Gly Asp Ser Asn Tyr Asp Glu
            325                330                335

Lys Leu Tyr Ile Asn Ala Leu Ser Pro Leu Leu Thr Ser Asn Gly Trp
        340                345                350

Pro Asn Ala His Phe Ile Met Asp Thr Ser Arg Asn Gly Val Gln Pro
    355                360                365

Thr Lys Gln Gln Ala Trp Gly Asp Trp Cys Asn Val Ile Gly Thr Gly
370                375                380

Phe Gly Val Gln Pro Thr Thr Asn Thr Gly Asp Pro Leu Glu Asp Ala
385                390                395                400

Phe Val Trp Val Lys Pro Gly Gly Glu Ser Asp Gly Thr Ser Asn Ser
            405                410                415

Ser Ala Thr Arg Tyr Asp Phe His Cys Gly Tyr Ser Asp Ala Leu Gln
        420                425                430

Pro Ala Pro Glu Ala Gly Thr Trp Phe Gln Ala Tyr Phe Val Gln Leu
    435                440                445

Leu Thr Asn Ala Asn Pro Ala Leu Val
450                455

<210> SEQ ID NO 2
<211> LENGTH: 2196
<212> TYPE: DNA
<213> ORGANISM: Acremonium cellulolyticus
<220> FEATURE:
<221> NAME/KEY: intron
<222> LOCATION: (320)..(389)
<220> FEATURE:
<221> NAME/KEY: intron
<222> LOCATION: (459)..(516)
<220> FEATURE:
<221> NAME/KEY: intron
<222> LOCATION: (800)..(869)
<220> FEATURE:
<221> NAME/KEY: intron
<222> LOCATION: (1124)..(1198)
<220> FEATURE:
<221> NAME/KEY: intron
<222> LOCATION: (1598)..(1651)

<400> SEQUENCE: 2

```
tgacgttact tcagactact cacgtgtcaa aagcagttag cgaggatcaa gtcttttagt    60
ctggtcatta acaaacgcaa tttcgcaacc cgataatccg cgatgataat atagcgactc   120
caaggtcgta tttatattca atcaattccc cccaatttgg aatggatttt tggaatcatc   180
gcatgccagg acaatcagtg aaacagtgac aaagtgaagc ttcttgatca tttagcaact   240
```

-continued

```
atgttgcgat atctttccat cgttgccgcc acggcaattc tgaccggagt tgaagctcag      300
caatcagtct ggggacaatg taagaagtct cttgagaagc ttcaagttaa gaataatcca      360
cggttgttga caatcttgga aacatatagg tggcggccaa ggctggtctg gcgcgacttc      420
atgcgccgcc ggttctacgt gcagcactct aaaccttgt aaggtgccag ctgattagta       480
tgttggctct gattcctgac gccaattgtt cattagacta cgcacaatgt atccctggta      540
ccgctacttc aactacattg gtgaaaacaa cgtcttctac cagcgtcgga acgacatcgc      600
cgccgacaac aaccacgacg aaagctagta ccactgctac taccactgcc gctgcatccg      660
gaaacccttt ctctggttac cagctttatg ccaatccgta ctattcttca gaagtacaca      720
ctcttgccat cccatctttg actggctcgc tcgctgctgc tgctaccaaa gctgccgaga      780
tcccctcatt tgtctggctg tgagtgttcc cgagaacatc cagttgagtg atataaatat      840
atgcatggag atttcctaaa cctctatagt gacacggcag ccaaagtgcc tacaatgggc      900
acctacttgg ccaacattga ggctgcaaac aaggctggcg ccagcccacc tattgccggt      960
atcttcgttg tctatgacct gcctgaccgt gactgtgcag ctgctgcaag taatggcgaa     1020
tacactgtag caaacaacgg tgttgcaaac tacaaggctt acatcgacag cattgtggca     1080
cagttgaaag cttatcccga tgtgcacaca atccttatca ttggtacgtt ctctactatt     1140
gggtcttgaa gaggtactct tgagagaaat ttgtgtctaa caaatcgccg atctacagag     1200
cctgatagtc tcgccaacat ggtcaccaat ctgtctacag ccaagtgtgc tgaggctcaa     1260
tctgcatact atgagtgcgt caactacgca ttgatcaacc tcaacttggc caacgtggcc     1320
atgtacattg atgctggtca tgctggttgg ctcggatggt ctgcgaatct ttcaccagcg     1380
gctcaactct tcgcaacagt ctataagaat gcaagtgccc ctgcatctct tcgtggattg     1440
gccaccaacg ttgccaacta caacgcttgg tcgatcagca gcccaccctc atacacatct     1500
ggcgactcca actacgacga aaagctctac atcaacgctt tgtctcctct cctgacatct     1560
aacggctggc ctaacgctca cttcatcatg gatacttgta agtgtgttgc ggatgaatca     1620
agtgctcggt ttactaactg aacttcttta gcccgaaacg tgttcaacc gactaagcag      1680 caggcatggg gtgactggtg caatgtgatc ggaaccggct tcggtgttca accgacaaca     1740
aatactggtg acccacttga ggatgccttt gtctgggtca agccaggtgg tgaaagtgat     1800
ggtacatcaa acagttccgc tactcgttac gatttccatt gcggctacag tgatgcactt     1860
caacccgccc ccgaggctgg gacttggttc caagcatact ttgtccagct tttgacaaat     1920
gccaacccag ctttggtcta gatcagcttt gagtgcagca aaaatgcttc cgactgtctt     1980
cttatattga tatcatattt ttcaattcac tttgtctcaa gtttcaatat atcgagaaaa     2040
tagtatcaaa gatgaactgt aataattccg atataccat acaggtttat agtaaattac      2100
tctatttcat aatgcgtcca tccgagaagt ctggcggcct tatcagtagt ccaaaacgcc     2160 tggttttag acatgtcacc tctaatctcc gcttga                                2196
```

<210> SEQ ID NO 3
<211> LENGTH: 9
<212> TYPE: PRT
<213> ORGANISM: Acremonium cellulolyticus
<220> FEATURE:
<221> NAME/KEY: UNSURE
<222> LOCATION: (6)
<223> OTHER INFORMATION: Xaa at position 6 is an amino acid

```
<400> SEQUENCE: 3

Ser Val Trp Gly Gln Xaa Gly Gly Gln
  1               5

<210> SEQ ID NO 4
<211> LENGTH: 7
<212> TYPE: PRT
<213> ORGANISM: Acremonium cellulolyticus

<400> SEQUENCE: 4

Ala Gln Ser Ala Tyr Tyr Glu
  1               5

<210> SEQ ID NO 5
<211> LENGTH: 5
<212> TYPE: PRT
<213> ORGANISM: Acremonium cellulolyticus
<220> FEATURE:
<221> NAME/KEY: UNSURE
<222> LOCATION: (3)
<223> OTHER INFORMATION: Xaa at position 3 is an amino acid

<400> SEQUENCE: 5

Gly Thr Xaa Phe Gln
  1               5

<210> SEQ ID NO 6
<211> LENGTH: 5
<212> TYPE: PRT
<213> ORGANISM: Acremonium cellulolyticus

<400> SEQUENCE: 6

Tyr Thr Val Ala Asn
  1               5

<210> SEQ ID NO 7
<211> LENGTH: 11
<212> TYPE: PRT
<213> ORGANISM: Acremonium cellulolyticus

<400> SEQUENCE: 7

Thr Ala Ala Lys Val Pro Thr Met Gly Thr Tyr
  1               5                  10

<210> SEQ ID NO 8
<211> LENGTH: 7
<212> TYPE: PRT
<213> ORGANISM: Acremonium cellulolyticus
<220> FEATURE:
<221> NAME/KEY: UNSURE
<222> LOCATION: (1)..(3)
<223> OTHER INFORMATION: Xaa at positions 1 and 3 is an amino acid

<400> SEQUENCE: 8

Xaa Pro Xaa Phe Val Trp Leu
  1               5

<210> SEQ ID NO 9
<211> LENGTH: 11
<212> TYPE: PRT
<213> ORGANISM: Acremonium cellulolyticus

<400> SEQUENCE: 9

Ala Tyr Ile Asp Ser Ile Val Ala Gln Leu Lys
  1               5                  10
```

```
<210> SEQ ID NO 10
<211> LENGTH: 12
<212> TYPE: PRT
<213> ORGANISM: Acremonium cellulolyticus
<220> FEATURE:
<221> NAME/KEY: UNSURE
<222> LOCATION: (7)
<223> OTHER INFORMATION: Xaa at position 7 is an amino acid

<400> SEQUENCE: 10

Asn Ala Trp Ser Ile Ser Xaa Pro Pro Ser Tyr Thr
 1               5                  10

<210> SEQ ID NO 11
<211> LENGTH: 17
<212> TYPE: DNA
<213> ORGANISM: Acremonium cellulolyticus
<220> FEATURE:
<221> NAME/KEY: modified_base
<222> LOCATION: (6)
<223> OTHER INFORMATION: n at position 6  is inosine

<400> SEQUENCE: 11
aargcntaya thgaytc                                                   17

<210> SEQ ID NO 12
<211> LENGTH: 17
<212> TYPE: DNA
<213> ORGANISM: Acremonium cellulolyticus
<220> FEATURE:
<221> NAME/KEY: modified_base
<222> LOCATION: (6)
<223> OTHER INFORMATION: n at position 6  is  inosine

<400> SEQUENCE: 12
aargcntaya thgayag                                                   17

<210> SEQ ID NO 13
<211> LENGTH: 17
<212> TYPE: DNA
<213> ORGANISM: Acremonium cellulolyticus
<220> FEATURE:
<221> NAME/KEY: modified_base
<222> LOCATION: (6)
<223> OTHER INFORMATION: n at position 6 is inosine
<220> FEATURE:
<221> NAME/KEY: modified_base
<222> LOCATION: (12)
<223> OTHER INFORMATION: n at position 12 is a, c, t or g

<400> SEQUENCE: 13
garatngacc angcrtt                                                   17

<210> SEQ ID NO 14
<211> LENGTH: 17
<212> TYPE: DNA
<213> ORGANISM: Acremonium cellulolyticus
<220> FEATURE:
<221> NAME/KEY: modified_base
<222> LOCATION: (6)
<223> OTHER INFORMATION: n at position 6  is  inosine
<220> FEATURE:
<221> NAME/KEY: modified_base
<222> LOCATION: (12)
<223> OTHER INFORMATION: n at position 12 is a, c, t or g

<400> SEQUENCE: 14
ctratngacc angcrtt                                                   17
```

-continued

```
<210> SEQ ID NO 15
<211> LENGTH: 17
<212> TYPE: DNA
<213> ORGANISM: Acremonium cellulolyticus
<220> FEATURE:
<221> NAME/KEY: modified_base
<222> LOCATION: (12)
<223> OTHER INFORMATION: n at position 12 is a, c, t or g

<400> SEQUENCE: 15
garatrctcc angcrtt                                                 17

<210> SEQ ID NO 16
<211> LENGTH: 17
<212> TYPE: DNA
<213> ORGANISM: Acremonium cellulolyticus
<220> FEATURE:
<221> NAME/KEY: modified_base
<222> LOCATION: (12)
<223> OTHER INFORMATION: n at position 12 is a, c, t or g

<400> SEQUENCE: 16
ctratrctcc angcrtt                                                 17

<210> SEQ ID NO 17
<211> LENGTH: 23
<212> TYPE: DNA
<213> ORGANISM: Acremonium cellulolyticus

<400> SEQUENCE: 17
ctgcatctct tcgtggattg gcc                                          23

<210> SEQ ID NO 18
<211> LENGTH: 24
<212> TYPE: DNA
<213> ORGANISM: Acremonium cellulolyticus

<400> SEQUENCE: 18
gattgtgtgc acatcgggat aagc                                         24

<210> SEQ ID NO 19
<211> LENGTH: 23
<212> TYPE: DNA
<213> ORGANISM: Acremonium cellulolyticus

<400> SEQUENCE: 19
ggtggtgaaa gtgatggtac atc                                          23

<210> SEQ ID NO 20
<211> LENGTH: 23
<212> TYPE: DNA
<213> ORGANISM: Acremonium cellulolyticus

<400> SEQUENCE: 20
aaagtcggta accagagaaa ggg                                          23

<210> SEQ ID NO 21
<211> LENGTH: 23
<212> TYPE: DNA
<213> ORGANISM: Acremonium cellulolyticus

<400> SEQUENCE: 21
ccaatccacg aagagatgca ggg                                          23
```

```
<210> SEQ ID NO 22
<211> LENGTH: 23
<212> TYPE: DNA
<213> ORGANISM: Acremonium cellulolyticus

<400> SEQUENCE: 22
gtgggatagc aaacaatatc cac                                    23

<210> SEQ ID NO 23
<211> LENGTH: 23
<212> TYPE: DNA
<213> ORGANISM: Acremonium cellulolyticus

<400> SEQUENCE: 23
ctttccatcg ttgccgccac ggc                                    23

<210> SEQ ID NO 24
<211> LENGTH: 23
<212> TYPE: DNA
<213> ORGANISM: Acremonium cellulolyticus

<400> SEQUENCE: 24
ctactaccac tgccgctgca tcc                                    23

<210> SEQ ID NO 25
<211> LENGTH: 24
<212> TYPE: DNA
<213> ORGANISM: Acremonium cellulolyticus

<400> SEQUENCE: 25
aatacactgt agcaaacaac ggtg                                   24

<210> SEQ ID NO 26
<211> LENGTH: 23
<212> TYPE: DNA
<213> ORGANISM: Acremonium cellulolyticus

<400> SEQUENCE: 26
caactacgac ccaagacacc ccg                                    23

<210> SEQ ID NO 27
<211> LENGTH: 24
<212> TYPE: DNA
<213> ORGANISM: Acremonium cellulolyticus

<400> SEQUENCE: 27
gtagccgcaa tggaaatcgt aacg                                   24

<210> SEQ ID NO 28
<211> LENGTH: 23
<212> TYPE: DNA
<213> ORGANISM: Acremonium cellulolyticus

<400> SEQUENCE: 28
tgctgagctt caactccggt cag                                    23

<210> SEQ ID NO 29
<211> LENGTH: 34
<212> TYPE: DNA
<213> ORGANISM: Acremonium cellulolyticus

<400> SEQUENCE: 29
gggaggcctg cgcatcatgt tgcgatatct ttcc                        34
```

```
<210> SEQ ID NO 30
<211> LENGTH: 32
<212> TYPE: DNA
<213> ORGANISM: Acremonium cellulolyticus

<400> SEQUENCE: 30
gggctcgagt accttagacc aaagctgggt tg                                    32
```